United States Patent [19]

Bijlenga

[11] 4,400,472

[45] Aug. 23, 1983

[54] NOVEL RABIES VIRUS STRAIN AND A PROCESS FOR ITS PREPARATION

[75] Inventor: Gosse Bijlenga, St. Didier au Mont d'Or, France

[73] Assignee: Gist-Brocades N.V., Delft, Netherlands

[21] Appl. No.: 310,447

[22] Filed: Oct. 13, 1981

Related U.S. Application Data

[62] Division of Ser. No. 872,056, Jan. 25, 1978, Pat. No. 4,320,115.

[30] Foreign Application Priority Data

Jan. 26, 1977 [GB] United Kingdom ............... 3258/77

[51] Int. Cl.$^3$ .......................... C12N 7/00; C12N 7/08
[52] U.S. Cl. .................................. 435/235; 435/237; 435/239
[58] Field of Search .................. 435/237, 239, 235

[56] References Cited

U.S. PATENT DOCUMENTS 3,397,267  8/1968  Fernandes ........................ 424/89

*Primary Examiner*—Sam Rosen
*Attorney, Agent, or Firm*—Hammond & Littell, Weissenberger and Muserlian

[57] ABSTRACT

A novel rabies virus strain No. 675 deposited in the Czechoslovak National Collection of Type Cultures of the Institute of Hygiene and Epidemiology in Prague under number CNCTO AO 4/77, novel living or inactivated cell culture vaccines derived therefrom, a process for the isolation of the virus strain as well as a process for the preparation of the said vaccines and novel method of immunizing warm-blooded animals against rabies.

3 Claims, No Drawings

NOVEL RABIES VIRUS STRAIN AND A PROCESS FOR ITS PREPARATION

PRIOR APPLICATION

This application is a division of my copending patent application Ser. No. 872,056 filed Jan. 25, 1978, now U.S. Pat. No. 4,320,115.

STATE OF THE ART

It is known to combat rabies viral infections in warm-blooded animals by preventive parenteral administration of vaccines such as LEP (Low Egg Passage) Flury or HEP (High Egg Passage) Flury vaccines which were obtained as described below.

On Jan. 29, 1939 a girl named Flury died in the State of Georgia with rabies being the diagnosed cause of death after infection by a rabid dog. The rabies virus was isolated from the brains, lachrymal gland and the salivary gland of the girl by means of intracerebral inoculation into white mice as described in Leach et al, [Amer. J. Trop. Med. (1949), Vol. 20 p. 335].

The brain material from the mice was inoculated intracerebrally into one day old chickens and 136 intracerebral passages in chickens were performed subsequently, according to Koprowski et al [J. Immunol. (1948), Vol. 60 p. 533]. After two additional intracerebral passages in chickens, the rabies virus was adapted to chicken embryos by a yolk-sac inoculation. After 60 yolk-sac passages, the virus appeared to be practically non-pathogenic for a number of mammals and is available at this serial passage level as rabies vaccine for dogs under the name of LEP Flury vaccine. After additional serial passages in chicken embryos (up to 170-174 passages), the virus appeared to have lost much more pathogenicity so that two week old laboratory mice were not killed after intracerebral administration although suckling mice were still killed. This vaccine is available under the name of HEP Flury vaccine (High Egg Passage Flury vaccine).

Although these LEP and HEP vaccines have been effective in preventing rabies infection when used as pre-exposure vaccines, the need for other rabies vaccines does exist as demonstrated by recent new control measures at the national and international level. For instance, the control of sylvatic rabies in developed countries where this disease has been endemic for a long time or where it has been introduced more recently is one of the difficult and ecologically complicated existing situations for which no effective and economical control method is available.

Also the post-exposure vaccine treatment of human beings has created numerous problems in rabies-infected countries throughout the world. For these reasons, research in rabies have been directed to the problems of post- and pre-exposure vaccination and immunization by a non-parenteral, preferably oral, route.

OBJECTS OF THE INVENTION

It is an object of the invention to provide a novel rabies strain and a novel process for the preparation thereof.

It is a further object of the invention to provide a novel rabies vaccine living or inactivated and to processes for obtaining the same.

It is an additional object of the invention to provide novel methods of immunizing warm-blooded animals against rabies.

These and other objects and advantages of the invention will become obvious from the following detailed description.

THE INVENTION

The novel rabies virus strain of the invention is No. 675 deposited in the Czechoslovak National Collection of Type Culture of the Institute or Hygiene and Epidemiology in Prague under number CNCTC AO 4/77 and is the most apathogenic existing rabies vaccine strain so far known. It offers the possibility of protection after exposure to street virus infection even using one single adequate dose of vaccine. The inactivated vaccine prepared from this strain 675 also protects after exposure, but to a lower degree. The living vaccine possesses a very high degree of antigenicity which is almost equalled by the inactivated type of vaccine. The living and inactivated vaccines are cell culture-type vaccines almost completely free from foreign proteins, which diminishes substantially, if not completely, the degree of undesirable side reactions.

The new virus strain was isolated as follows: The virus of the HEP Flury vaccine was propagated in primary or secondary SPF chicken embryo fibroblasts and was also identified as rabies virus with the aid of specific immunofluorscence of those infected fibroblasts, by a mouse protection test through intraperitoneal vaccination followed by the administration of a standardized rabies challenge virus (CVS) and by in vitro seroneutralization tests with known positive serum (International Rabies Reference Serum).

It will be appreciated that for the propagation of the starting HEP Flury vaccine also other rabies susceptible cell lines and diploid cell strains may be applied instead of the SPF chicken embryo fibroblasts.

By the use of the plaque assay method in chicken embryo fibroblasts (SPF) according to Yoshina et al, [Arch. ges. Virusforsch., (1966), Vol. 18 p. 370] and the plaquing cell suspension method according to Bijlenga et al., [Bull. Soc. Sci. Vet. et Med. Comparee, Lyon, (1974), Vol. 76, p. 429], it was possible to isolate a plaque which clearly differed from the starting virus population in its cytopathic effect on the infected cells. This plaque was cloned three times in order to obtain a homogeneous and pure virus population.

The originally isolated plaque was allocated the number 675 and the strain after purification as rabies vaccine strain No. 675. A sample of this strain was deposited with the Czechoslovak National Collection of Type Cultures of the Institute or Hygiene and Epidemiology in Prague on 13th January 1977, and is recorded there under CNCTC Number AO 4/77.

The strain can be distinguished from the original HEP Flury virus in respect of the following characteristics: (a) A very pronounced cytopathic effect on in vitro cell cultures, an effect which is not caused by the HEP Flury virus: (b) Shortened primary virus cycle, varying between 9 and 11 hours, causing a more rapid appearance of plaques; (c) Very clear plaques, which are on the average somewhat larger (1 mm larger) in diameter than the plaques of the HEP virus; (d) Enchanced attaching capacity to the surface of cells in vitro, which characteristic is essential for an adequate oral vaccine; (e) Faster production of interferon in vivo after vaccination because of the properties as mentioned hereinbefore. This property is important for post-exposure vaccination; (f) Higher titers are obtained in cell cultures; (g) By clone purification, homogeneous virus populations are obtained resulting in a decreased risk of possible reversion of the virus strain to its original virulence, which reversion may be practically excluded. (h) It is the most apathogenic rabies strain so far available.

It will be appreciated that these characteristics as indicated under (a–h) show a clear cut distinction from the original HEP Flury virus. It will also be appreciated that the present invention includes within its scope artificial mutant strains derived from virus strain No. 675 and having the properties of strain No. 675 described above. Due to the above mentioned characteristics, particularly (g), the preparation of vaccine batches having a constant quality is facilitated, i.e. vaccines of improved consistency can be prepared according to the invention from the virus strain No. 675.

The vaccines which form another feature of the present invention show the following advantages: (1) As with the original HEP Flury vaccine, the line virus vaccine of the invention does not multiply after administration and no residual virus can be detected; (2) The vaccines caused very rapid interferon production and other additional, unknown interfering properties, e.g. cellular mediated immunity. A single administration of vaccine after experimental infection with a naturally occuring virus can provide full protection.

In view of the very rapid production of interferon and cellular mediated immunity, the application of the vaccines of the invention for the protection of recently exposed animals during outbreaks of rabies is now feasible. Particularly, the possiblity of post-exposure vaccine treatment of humans has been improved considerably as the vaccines have been shown to be highly effective in animals after exposure to infection and can even cure animals in a very advanced state of infection. (3) Non-parenteral administration e.g. by the oral route of the live vaccine, facilitates its use in organized vaccination compaigns.

The living type of this vaccine is very suitable for oral administration. Oral administration is desirable for the immunization (to be called hereinafter "oral vaccination") of eg. foxes. Oral and other non-parenteral routes of administration such as intestinal or intranasal administration by spray, to other epidemiologically important wild animals, to domestic animals and human beings, also form a feature of this invention.

The new strain can be administered by different routes, i.e. which can be administered parenterally or non-parenterally, and which appears to provide a full protection when administered before or after a rabies infection. The possibility of effective oral administration with the aim of achieving "oral vaccination" of wild animals, who are the most important vectors and/or sources of rabies, will be appreciated as an advantageous feature of the present invention.

The live virus vaccine prepared form strain 675 has the following possible advantages for pre-exposure vaccination:

(A) In animals: 1. Immunization of foxes and other epidemiologically important wild animals with the aid of rabies vaccine-containing baits. 2. Oral vaccination of domestic animals, for instance stray dogs, in countries where killing them is prohibited on religious and/or legislative grounds. 3. Large scale administration of the live virus vaccine by means of baits so that vaccination campaigns can be markedly simplified. For instance, distribution of optionally frozen meat balls containing virus vaccine by aircraft. 4. Effective protection of domestic animals after exposure for use in countries wherein such vaccination procedures are authorized and in countries where animals can be kept after exposure provided they already had been immunized.

(B) In humans: 1. Fear of oral vaccination is negligible. Fear of inoculation is a very important factor in several countries and causes a reduction in the number of patients who return for the required number of inoculations. 2. Administration per os does not cause local reactions or irritations which form a real disadvantage for presently commercially available, prior art vaccines. 3. Easy administration on a large scale and by non-medically trained personnel has become possible (cf. oral poliomyelities vaccination). In this connection, the fact that one single administration of the vaccine has appeared to be sufficient will be appreciated as important.

For instance, the inactivated vaccines of the present invention may be effectively applied to humans for pre-exposure vaccination by administration of one dose of 1 ml, when the titer of the vaccine before inactivation is about $10^{7.5}$ pfu/ml. Repetition of this vaccination may be necessary every year when infection may occur. The same dose of this inactivated vaccine of the same original titer may be administered to humans for post-exposure vaccination on the day of infection and 1,3 and 7 days thereafter for satisfactory results.

The novel vaccines are prepared by usual procedures, i.e. in vitro cell cultures, by application of the usual and prescribed controls to eliminate bacterial and/or viral contaminations, according to the well known principles and international standard requirements.

The novel vaccines of the invention are preferably prepared by growing the rabies virus in monolayers of primary or secondary chicken embryo fibroblasts derived from SPF 10 day old chicken embryos. However, other cell systems which are sufficiently susceptible to rabies infection can also be used such as other cells of avian origin or mammalian cells, e.g. the Baby Hamster Kidney 21 (21 passages) for monolayer culture or the BHK-21 13 S (13 passages of suspension culture) for suspended culture, but in this case only for animal vaccines. The suspended cell culture system has the great advantage of permitting production of the virus vaccines in fermenters of large capacity which facilitates production.

The vaccines can also be prepared in cells grown on micro carriers (bead cell-culture system). For example, poly dextran beads treated with macromolecular anions prior and/or during cell growth may be used having an adequate positive charge density for cell growth on their surface. In this way, a stirred suspension of cells and beads in a liquid medium would be inoculated with the desired virus and after propagation of the virus, the beads are sunk to the bottom of the reactor and separated from the suspension of viruses.

In a specific method for the preparation of the vaccines, the chicken embryo fibroblasts are infected with the rabies seed virus strain No. 675 having a multiplicity of infection of 0.02 to 1 pfu/cell with an infection period of at least one hour being preferred. After removal of the unattached virus, a maintenance medium is added, preferably consisting of Basal Medium Eagle (BME) in Earle's salt solution to which appropriate amounts of antibiotics and 0.2 to 0.5% of albumin are added. Care must be taken to ensure that the pH of the maintenance medium is kept at 8.0 to 8.2 The virus-infected cells are incubated at 32°–39° C. for 3 to 10 days and the medium is then frozen at −70° C. or below to disrupt the cells and release the virus, thereby increasing the titre. The cells and cell debris are removed by filtration or centrifugation under sterile conditions. The filtrate or supernatant liquid is stored at −70° C. and samples are taken for titration purposes by the in vitro plaquing method referred to above. It will be appreciated that other methods may be used to disrupt the cells after incubation e.g. by subjecting the cell suspension to ultrasonic vibration.

According to an alternative specific preparation method BHK-21 13S cells are grown in suspension, e.g. in a spinner flask with hanging bar, using BHK-21 medium for spinner culture to which small amounts of tryptose phosphate broth (7–15%) inactivated calf serum (7–15%) and antibiotics, such as 100 IU of penicillin and 100 micrograms of streptomycins, are added. The cells are grown until about a level of $2 \times 10^6$ cells/ml is reached, while the cells are agitated sufficiently to keep them in suspension and to avoid clumping together. After spinning down the cells by a centrifuge, infection with rabies seed virus strain 675 in a multiplicity of infection between 0.01 and 1 is performed for 30 to 60 minutes with constant stirring.

After infection, the cells are suspended again in the spinner flask and maintenance medium consisting of BHK-21 spinner culture medium to which small amounts of bovine serum albumin fraction V (e.g. 0.1–0.4%) and antibiotics such as kanamycin or neomycin (in an amount of e.g. 50–300 micrograms) are added along with an adjustment of the pH between 7.5 and 8.0. During the infection, the temperature is kept at 32° to 35° C. and preferably at 33° C. and every day a small sample of the spinner flask is removed for examination by the immunofluorescent technique. Between 2 to 3 days after infection, 80 to 100% of the cells in these samples will show a specific immunofluoresence for rabies inclusion bodies in their cytoplasm, corresponding to a titer of $10^8$ to $10^9$ pfu/ml at harvest on 4 to 6 days after infection. At harvest, the liquid is removed from the flask and stored frozen at −70° C.

A small sample is titrated after removing the cells and cell debris by the plague titration method. If an acceptable titer was reached (between $10^{7.5}$ and $10^{8.5}$ pfu/ml or higher), the cells and cell debris are removed from the harvest by filtration or centrifugation under sterile conditions. After addition of a suitable stabilizer, the fluid is ready e.g. for distribution in vials for lyophilization of the final product.

It will be appreciated that also killed (inactivated) rabies vaccines, preferably for human use, are included within the scope of the invention. These killed rabies vaccines may be prepared by inactivating the virus in the prepared culture fluids by known procedures or modifications thereof, e.g. by addition of beta-propiolactone, formalin or acetylethyleneimine, or by ultraviolet irradiation. It will be appreciated that rabies vaccines which are derived from the virus strain of the invention may contain one or more suitable stabilizers, preservatives, buffering salts and adjuvants.

In the following examples there are described several preferred embodiments to illustrate the invention. However, it is to be understood that the invention is not intended to be limited to the specific embodiments.

EXAMPLE 1

Monolayers of primary or secondary SPF chicken embryo fibroblasts grown in stationary or roller bottles were infected with the rabies seed virus strain 675 having a multiplicity of infection (m.o.i.) of 0.02 to 1 pfu/cell. Lower amounts of virus could also be used but the incubation period was then prolonged. An infection period of at least one hour was required for attachment of the seed virus to the cells. Then, the remaining unattached virus was removed and the maintenance medium was added, consisting of Basal medium Eagle (BME) in Earle's salt solution to which appropriate amounts of antibiotics and 0.2% of albumin of the relevant species for which the vaccine is to be used were added, taking care that the final mixture of the maintenance medium had a pH of 8.2.

Incubation at 33° to 35° C. for 4 to 8 days of the virus infected cells resulted in a pronounced CPE (cytopathic effect) and the medium was then frozen at −70° C. Cells and cell debris were removed, after thawing of the product by centrifugation at 1,000 g's or by filtration through a membrane filter (5 microns pore size) under sterile conditions. The fluid, either supernatant or filtrate, was stored at −70° C. and samples were taken for titration purposes by the in vitro plaquing method previously mentioned (Bijlenga and Joubert).

Accepted titers for vaccine batches to be used for effective vaccination after exposure were $10^8$ pfu/ml. For pre-exposure vaccination, minimum titers up to $10^7$ pfu/ml were still acceptable.

The production of vaccine batches as described above was controlled by the usual potency tests (NIH and Habel test) and for the batches to be used for post-exposure treatment an additional new potency test of Bijlenga [Symposium on Advances in Rabies Research, Atlanta, Georgia, Sept. 7-9, 1976, page 14] was included. In this new potency test, local street virus was administered intramuscularly (i.m.) to 4 week old mice, followed by a single intraperitoneal inoculation of 0.5 ml vaccine within 24 hours. All vaccinated mice should survive, whereas approximately 50% of the control mice should be dead before the end of the 3 week testing period. Also, the usual controls for sterility tests for possible bacterial and viral contamination of the vaccine batches, together with the procedures for the control of primary or secondary cells and cell lines employed for the production of the vaccines were followed according to internationally established minimum requirements.

EXAMPLE 2

BHK-21 13 S cells was grown in suspension in a Bellco spinner flask with hanging bar using BHK-21 medium for spinner culture to which 10% tryptose phosphate broth and 10% inactivated calf serum were added in the presence of antibiotics (100 IU of penicillin and 100 micrograms of streptomycin). The cells were grown until a level of $2\times10^6$ cells/ml was reached while the cells were agitated sufficiently to keep them in suspension and to avoid clumping together.

After spinning down the cells at 800 rpm by a centrifuge, infection with rabies seed virus strain 675 in a multiplicity of infection between 0.01 to 1 was performed for 45 minutes with constant stirring. After infection, the cells were suspended again in the spinner flask and maintenance medium consisting of BHK-21 spinner culture medium to which 0.2% of bovine serum albumin fraction V was added together with appropriate amounts of acceptable antibiotics (i.e. kanamycin or neomycin), along with an adjustment of the pH at 7.8. During infection, the temperature was kept at 33° C. and every day a small sample of the spinner flask was removed for examination by the immunofluorescent technique. Between two to three days after infection, 80 to 100% of the cells in these samples showed a specific immunofluorescence for rabies inclusion bodies in their cytoplasm, which in turn guarantees an adequate titer of $10^8$ to $10^9$ pfu/ml at harvest 4 to 6 days after infection. At harvest, the liquid was removed from the flask and stored frozen at $-70°$ C. A small sample of the harvest was kept separately for titration after removal of the cells and cell debris by the plaque titration method. If the titer is acceptable (between $10^{7.5}$ and $^{8.5}$ pfu/ml or higher), the cells and cell debris were removed from the harvest as described previously and the fluid was ready, after adding a suitable stabilizer, for distribution into vials for lyophilization of the final product.

An alternative method to obtain even higher titers can be employed by infecting either stationary complete monolayers or such monolayers in roller culture bottles. Between two and eight hours after infection, the cells were trypsinized and put into suspension culture as described above. Care should be taken that no cell clumping occurs. In this way, more than $2\times10^6$ cells/ml can be employed which gives higher titers of the harvest depending upon the number of infected cells put into suspension culture.

EXAMPLE 3

To demonstrate the use and value of the living and the inactivated rabies vaccines of the invention, results of pre- and post-exposure vaccination experiments are listed below:

A. Oral vaccination of foxes with live rabies vaccine strain 675 (2 ml/fox) the titer of the vaccine being $2\times10^8$ pfu/ml.

| | age at time of | | | | |
|---|---|---|---|---|---|
| Identi-fication | vaccin-ation | serum titer in IU* | | | challenge** |
| No. of foxes | Aug. 11 | Sept. 11 | Oct. 7 | Nov. 21 | Dec. 23 |
| Orally | 84 | 5 months | 4.0 | 7.0 | 8.2 | protected |
| Vaccinated | 86 | 6 months | 1.3 | 1.6 | 1.4 | protected |
| Animals | 88 | 6 months | 2.0 | 2.4 | 3.2 | protected |
| controls | 83 | 6 months | | | | dead after 15 days |
| (non-vaccinated | 85 | 6 months | | | | dead after 17 days |
| animals) | 92 | 6 months | | | | dead after |

-continued

| Identi-fication | age at time of vaccin-ation | serum titer in IU* | | | challenge** |
|---|---|---|---|---|---|
| No. of foxes | Aug. 11 | Sept. 11 | Oct. 7 | Nov. 21 | Dec. 23 |
| | | | | | 18 days |

*One I.U. (International Unit) = a serum dilution of 1/300 which dilution gives a 50% plaque reduction endpoint reading.
**A very high dose of challenge virus (from salivary gland of naturally infected fox), namely 1,391,610 $MLD_{50}$, was used for testing the protective value of the vaccine.

This experiment shows the effectiveness of oral vaccination of young foxes. The immunity responses of the foxes demonstrate an adequate seroconversion and good titers. More than five months after vaccination, the three foxes were fully protected and all three control foxes died within very short incubation periods which was due to the very high dose of the challenge virus inoculated intramuscularly in the right hind leg. The usual challenge dose for foxes employed was 3,000 $MLD_{50}$.

B. Serological results after vaccination with inactivated strain 675

| Species of animal | Weight of animals in kg | dose in ml | Serum titers 4 weeks after vaccination |
|---|---|---|---|
| Dog | | | |
| 1 | 6.5 | 2 i.m. | 6.8 |
| 2 | 8 | 2 i.m. | 6.3 |
| 3 | 12 | 2 i.m. | 5.5 |
| 4 | 10 | 2 i.m. | 12.3 |
| 5 | 15 | 2 i.m. | 5.9 |
| 6 | 14 | 2 i.m. | 4.5 |
| 7 | 17 | 2 i.m. | 3.8 |
| 8 | 17 | 2 i.m. | 20.5 |
| Cow | | | |
| 1 | 200 | 5 s.c. | 4.5 |
| 2 | 400 | 5 s.c. | 8.5 |
| 3 | 300 | 5 s.c. | 15.5 |
| 4 | 500 | 5 s.c. | 4.8 |
| 5 | 400 | 5 s.c. | 7.6 |
| 6 | 600 | 5 s.c. | 8.9 |
| 7 | 500 | 5 s.c. | 3.8 |
| 8 | 400 | 5 s.c. | 4.7 |

One single injection of vaccine was administered and the indicated titers were expressed in I.U. as in the previous Table.

At four weeks after vaccination, the eight dogs and eight cattle all showed a seroconversion with very high titers. The minimum titer required for seroconversion was established by the European Pharmacopee at a level of 0.2 I.U./ml.

C. Protection of laboratory mice after infection with wild live virus (of fox origin)

| Type of vaccine | Interval between infection and vaccination | | | | | | | | |
|---|---|---|---|---|---|---|---|---|---|
| | 1 hour | 1 day | 2 days | 3 days | 4 days | 5 days | 6 days | 7 days | 8 days | 9*** days |
| Living vaccine 675* | | | | | | | | | | |
| Undiluted | —0/10** | 1/10 | 1/10 | 1/10 | 2/10 | 0/10 | 0/10 | 4/10 | 5/10 | 3/10 |
| $10^{-1}$ | 1/10 | | | | | | | | | |
| $10^{-2}$ | 4/10 | | | | | | | | | |
| $10^{-3}$ | 6/10 | | | | | | | | | |
| $10^{-4}$ | 8/10 | | | | | | | | | |
| Controls | 6/10 | 8/10 | 7/10 | 7/10 | 7/10 | 7/10 | 6/10 | 6/10 | 6/10 | 8/10 |

-continued

| Type of vaccine | Interval between infection and vaccination | | | | | | | | |
|---|---|---|---|---|---|---|---|---|---|
| | 1 hour | 1 day | 2 days | 3 days | 4 days | 5 days | 6 days | 7 days | 8 days | 9*** days |
| Inactivated vaccine 675* | | | | | | | | | |
| Undiluted | 0/10 | 1/10 | 5/10 | | | | | | |
| $10^{-1}$ | 1/10 | | | | | | | | |
| $10^{-2}$ | 6/10 | | | | | | | | |
| $10^{-3}$ | 8/10 | | | | | | | | |
| $10^{-4}$ | 6/10 | | | | | | | | |

*Titer of vaccine $10^{8.2}$ pfu/ml (for inactivated vaccine the titer was determined before inactivation)
**number of deaths/number of inoculated mice.
***Two vaccinations (at day 9 and 11)

All mice listed in this table were inoculated intramuscularly with a fox salivary gland rabies virus (0.1 ml of solution) which killed 60–80% of the controls with an incubation period of 9 to 11 days. The living and the inactivated vaccine strain 675 were administered in one single dose (0.5 ml) intraperitoneally at various periods after the initial infection as indicated in the Table. The living undiluted vaccine protected still 6 days after infection which has never been observed before for any other commercial vaccine available. This protection showed that even after the rabies virus had reached the central nervous system, the mice can still be cured. With two vaccinations at one day interval and starting nine days after infection, some of the mice were still protected.

This living vaccine could also be diluted up to ten times and afforded protection but not longer than at 24 hours after infection. The inactivated vaccine protected only when applied within the 24 hours after infection and could also be diluted but not more than ten times.

Various modifications of the vaccine and strains and processes of the invention may be made without departing from the spirit or scope thereof and it should be understood that the invention is to be limited only as defined in the appended claims.

I claim:

1. A rabies virus strain exhibiting reproducibly significant cytopathic effect on in vitro cell cultures of primary or secondary SPF chicken embryo fibroblasts of strain No. 675 deposited with the Czechoslovak National Collection of Type Culture of the Institute of Hygiene and Epidemiology in Prague deposited under CNCTC AO 4/77.

2. A process for the preparation of live rabies virus of